United States Patent [19]

Buote

[11] Patent Number: 5,450,743
[45] Date of Patent: Sep. 19, 1995

[54] METHOD FOR PROVIDING CONSTANT FLOW IN LIQUID CHROMATOGRAPHY SYSTEM

[75] Inventor: William J. Buote, Natick, Mass.

[73] Assignee: Zymark Corporation, Hopkinton, Mass.

[21] Appl. No.: 179,406

[22] Filed: Jan. 10, 1994

[51] Int. Cl.$^6$ .................. G01N 30/32; G01N 30/36; F04B 49/12; F04B 49/20
[52] U.S. Cl. ........................ 73/61.56; 210/137; 210/198.2; 417/18; 417/22
[58] Field of Search ............... 73/61.56, 61.57, 864.35, 73/864.81; 210/103, 137, 198.2; 417/15, 22, 43, 18

[56] References Cited

U.S. PATENT DOCUMENTS

| | | | |
|---|---|---|---|
| 3,847,507 | 11/1974 | Sakiyama et al. | 417/22 |
| 3,985,021 | 10/1976 | Achener et al. | 73/61.56 |
| 4,137,011 | 1/1979 | Rock | 417/22 |
| 4,233,156 | 11/1980 | Tsukada et al. | 73/61.56 |
| 4,448,692 | 5/1984 | Nakamoto et al. | 417/18 |
| 4,767,279 | 8/1988 | Dovrdeville et al. | 417/18 |
| 4,797,207 | 1/1989 | Honganen et al. | 417/18 |
| 4,919,595 | 4/1990 | Likuski et al. | 417/22 |
| 4,980,059 | 12/1990 | Barlow et al. | 210/137 |
| 5,108,264 | 4/1992 | Abdel-Rahman | 417/22 |

Primary Examiner—Hezron E. Williams
Assistant Examiner—Michael J. Brock
Attorney, Agent, or Firm—John E. Toupal; Harold G. Jarcho

[57] ABSTRACT

A method of operating liquid chromatography apparatus. The method includes the steps of determining a given rate of liquid flow desired from a piston pump to the column; establishing for the piston a predetermined stroke length and rate of reciprocation for providing the given rate of liquid flow; determining for each cycle of the pump a desired liquid volume that would be delivered to the column by the pump if producing the given rate of liquid flow; ascertaining for each cycle of the pump the actual liquid volume delivered thereby to the column; determining for a predetermined operating period of the pump the total desired liquid volume that would have been delivered to the column by the pump if producing the given rate of liquid flow during each cycle of the predetermined operating period; and determining the total actual liquid volume delivered to said column by said pump during all cycles of said predetermined operating period. After comparing the total desired liquid volume with the total actual liquid volume one or more subsequent piston cycles are produced that provide a compensating liquid flow rate different than the given rate of liquid flow in response to a determination during the comparing step that a difference exists between the total actual liquid volume and the total desired liquid volume. The compensating rates of liquid flow correct pumping cycle errors that produce incorrect liquid volume flow.

28 Claims, 5 Drawing Sheets

METHOD FOR PROVIDING CONSTANT FLOW IN LIQUID CHROMATOGRAPHY SYSTEM

BACKGROUND OF THE INVENTION

This invention relates generally to a high pressure liquid chromatography (HPLC) solvent delivering system and, more particularly, to an HPLC system capable of delivering constant flow of solvent mass.

HPLC solvent delivery systems have the primary objective of delivering constant flow of solvent mass through an HPLC column. Many HPLC systems utilize a single piston plunger pump that runs in a "open loop" mode with no measurements of actual solvent conditions. Under ideal conditions, a single piston plunger pump can deliver relatively constant flow over the long term, but produces individual cycles of fluctuating flow. The fluctuations in solvent flow usually result from variations in the time periods required during a given pump cycle for compression of liquid solvent prior to delivery and for full decompression of the pumping chamber after a delivery period. Factors affecting the lengths of the compression and decompression periods include the inadvertent presence in the pumping chamber of gasses, system leaks and changes in solvent compressibility. The presence of gasses in the pumping chamber may completely prevent solvent delivery, but in all cases produces an error in delivery volume that is undetectable by the pump.

Because of the difficulty of controlling mass flow directly, existing HPLC systems typically rely on precision manufacture of volumetric chambers, precision control of reciprocating displacement plungers, and carefully controlled conditioning of the solvents being pumped. Solvent conditioning reduces the possibility of developing gasses in a pumping chamber while precision manufacture of chambers and position control of reciprocating plungers enhances the predictability of pump delivery volume. For example, attempts are often made to minimize a pump's dead volume and thereby reduce flow delivery errors that occur during a pump's decompression period. However, dead volume can not be fully eliminated with practical methods and in any case there are numerous advantages to the use of a variable displacement pump which inherently exhibits dead volume.

An early improvement in HPLC systems employed a pair of interconnected piston pumps having piston plungers that operated with overlapping motions to thereby substantially smooth plunger cycle variations. However, the overlapped plunger motion of such systems can only be optimized for single solvent compressibility, and the systems retain a requirement for highly controlled conditioning of solvent to prevent the appearance of gasses.

A more recent HPLC system claiming improved solvent flow characteristics is disclosed in U.S. Pat. No. 4,919,595. That system included in a pumping chamber a pressure transducer to provide pressure information used to determine the loss of solvent flow that occurs during refill and compression periods of a pump cycle. The measured volume of deficit flow then is introduced to the system by increasing the velocity of the piston plunger during that period of a delivery stroke immediately following a refill stroke. Although compensating for deficit flow, the disclosed system doesn't consider the presence of gas in the pump and consequently requires careful conditioning of solvent because flow compensation is limited to the volume of surplus flow in the remaining stroke of the piston plunger. In an extreme case of a large gas bubble being ingested by the pump, an entire cycle can be completed compressing only gas and resulting in no deficit flow compensation.

Many HPLC systems employing single piston plunger pumps utilize a pulse damper to smooth the flow of solvent to a column. The damper accumulates solvent during the pump's delivery stroke and delivers solvent during the pump's refill stroke. Although improving the long term flow characteristics of the system, the solvent flow versus time output characteristic of a damper is a saw-tooth function in which solvent flow cyclically varies above and below average flow for the system. The cyclical periods of non-average flow are detrimental to chromatographic analysis.

The object of this invention, therefore, is to provide an improved HPLC system that alleviates the above described problems.

SUMMARY OF THE INVENTION

The invention is a method of operating liquid chromatography apparatus including a piston pump having a piston reciprocable within a chamber, an inlet valve for transmitting liquid into the chamber, an outlet valve for discharging liquid from the chamber, a separation column receiving liquid from the outlet valve, pressure detection means for monitoring the pressure in the chamber, a variable speed drive for inducing reciprocating movement of the piston, position detection means for monitoring the position of the piston in the chamber and a computer control for controlling the stroke length and reciprocating velocity of the piston. The method includes the steps of determining a given rate of liquid flow desired from the pump to the column; establishing for the piston a predetermined stroke length and rate of reciprocation for providing the given rate of liquid flow; determining for each cycle of the pump a desired liquid volume that would be delivered to the column means by the pump if producing the given rate of liquid flow; ascertaining for each cycle of the pump the actual liquid volume delivered thereby to the column; determining for a predetermined operating period of the pump the total desired liquid volume that would have been delivered to the column by the pump if producing the given rate of liquid flow during each cycle of the predetermined operating period; and determining the total actual liquid volume delivered to said column means by said pump during all cycles of said predetermined operating period. After comparing the total desired liquid volume with the total actual liquid volume one or more subsequent piston cycles are produced that provide a compensating liquid flow rate different than the given rate of liquid flow in response to a determination during the comparing step that a difference exists between the total actual liquid volume and the total desired liquid volume. The compensating rates of liquid flow correct pumping cycle errors that produce incorrect liquid volume flow.

According to one feature of the invention, the operating period comprises a single cycle by the pump. In this case, each cycle is analyzed for errors which are corrected in subsequent cycles.

According to another feature of the invention, the comparing step includes the steps of comparing during each cycle of the predetermined operating period the desired liquid volume with the actual liquid volume, and algebraically summing the differences therebetween for all the cycles to thereby determine the error difference to be corrected. By summing only the detected flow difference less computer memory is required.

According to yet another feature of the invention, the subsequent cycles are continued until a comparing step determines that the total actual liquid volume is equal to the total desired liquid volume. At that time no further compensation is required.

According to still another feature of the invention, the producing step includes for each subsequent cycle the step of providing a stroke length different than the predetermined stroke length. Compensating flow rates are easily provided by change in stroke length.

According to further features of the invention, the producing step includes the steps of providing a stroke length longer than the predetermined stroke length in response to a determination that the total actual liquid volume is less than the total desired liquid volume and a stroke length shorter than the predetermined stroke length in response to a determination that the total actual liquid volume is greater than the total desired liquid volume. Proper correction is provided by these parameters.

According to yet another feature of the invention, the producing step further includes for each subsequent cycle the step of changing the reciprocation velocity of the one piston so as to maintain the predetermined rate of reciprocation. In this way a desired reciprocation rate is maintained.

According to an additional feature of the invention, the ascertaining step includes the step of ascertaining for each cycle the volume of liquid at atmospheric pressure delivered by the pump to said column means. Determination of actual volume is simplified at atmospheric pressure.

According to further features, during each operating cycle, the piston completes a positive stroke including a gas compression stroke period during which any gas in the chamber is compressed while the outlet valve and the inlet valve are closed, a liquid compression stroke period during which liquid in the chamber is compressed while the outlet valve and the inlet valve are closed and a delivery stroke period during which liquid is delivered to the column while the outlet valve is open and the inlet valve is closed; and a return stroke including a liquid decompression stroke period during which liquid in the chamber is decompressed while the outlet valve and the inlet valve are closed, a gas decompression stroke period during which any gas in the chamber is decompressed while the outlet valve and the inlet valve are closed, and an intake stroke period during which liquid is received by the chamber while the outlet valve is closed and the inlet valve is open.

According to other features, the inlet valve is a valve that closes in response to a pressure in the chamber above atmospheric and opens in response to above atmospheric pressure in the chamber; and the ascertaining steps include the step of calculating an effective length of the return stroke during which liquid at atmospheric pressure is received by the chamber. Actual delivered volume is provided by this information.

According to further features, the calculating step includes the steps of calculating the length of the delivery stroke period plus the length of the liquid compression stroke period less the length of the liquid decompression stroke period, and determining the lengths of the gas compression and the gas decompression stroke periods. These steps facilitate determination of the effective length of the return stroke.

According to additional features, the calculating steps include the steps of correlating detected pressures in the chamber with positions of the piston during the gas and liquid compression stroke periods and during the gas and liquid decompression stroke periods, and finding a substantially linear progression of the information derived during the correlating steps. These steps further facilitate a determination of the return strokes effective length.

The invention also encompasses a method of operating liquid chromatography apparatus of the above featured type and including a damper receiving liquid from the outlet and including the steps of: determining a given rate of liquid flow to the column; determining for the piston a predetermined velocity for provided the given rate of liquid flow; detecting a delivery period during which the outlet valve is delivering liquid from the chamber; establishing for the piston during an initial portion of the delivery period a first velocity substantially greater than the predetermined velocity; establishing for the piston during a final portion of the delivery period a second velocity substantially greater than the predetermined velocity; and establishing for the piston during an intermediate portion of said delivery period the predetermined velocity. Together with the damper these features facilitate establishment of a substantially uniform flow rate.

According to another feature of the immediately above invention, the establishing steps produce a first volume increase in the damper during the initial portion of the delivery period, substantially no volume change in the damper during the intermediate portion of the delivery period, and a second volume increase in the damper during the final portion of said delivery period, the first velocity is substantially equal to the second velocity, and the first volume increase is substantially equal to the second volume increase. These features provide for substantially contact flow at a desired value.

According to another feature, the final portion of the delivery period is longer than the initial portion of the delivery period. This feature compensates for the decreased damper output during the final delivery period.

DESCRIPTION OF THE DRAWINGS

These and other objects and features of the invention will become more apparent upon a perusal of the following description taken in conjunction with the accompanying drawings wherein.

DESCRIPTION OF THE PREFERRED EMBODIMENTS

Figure 1:
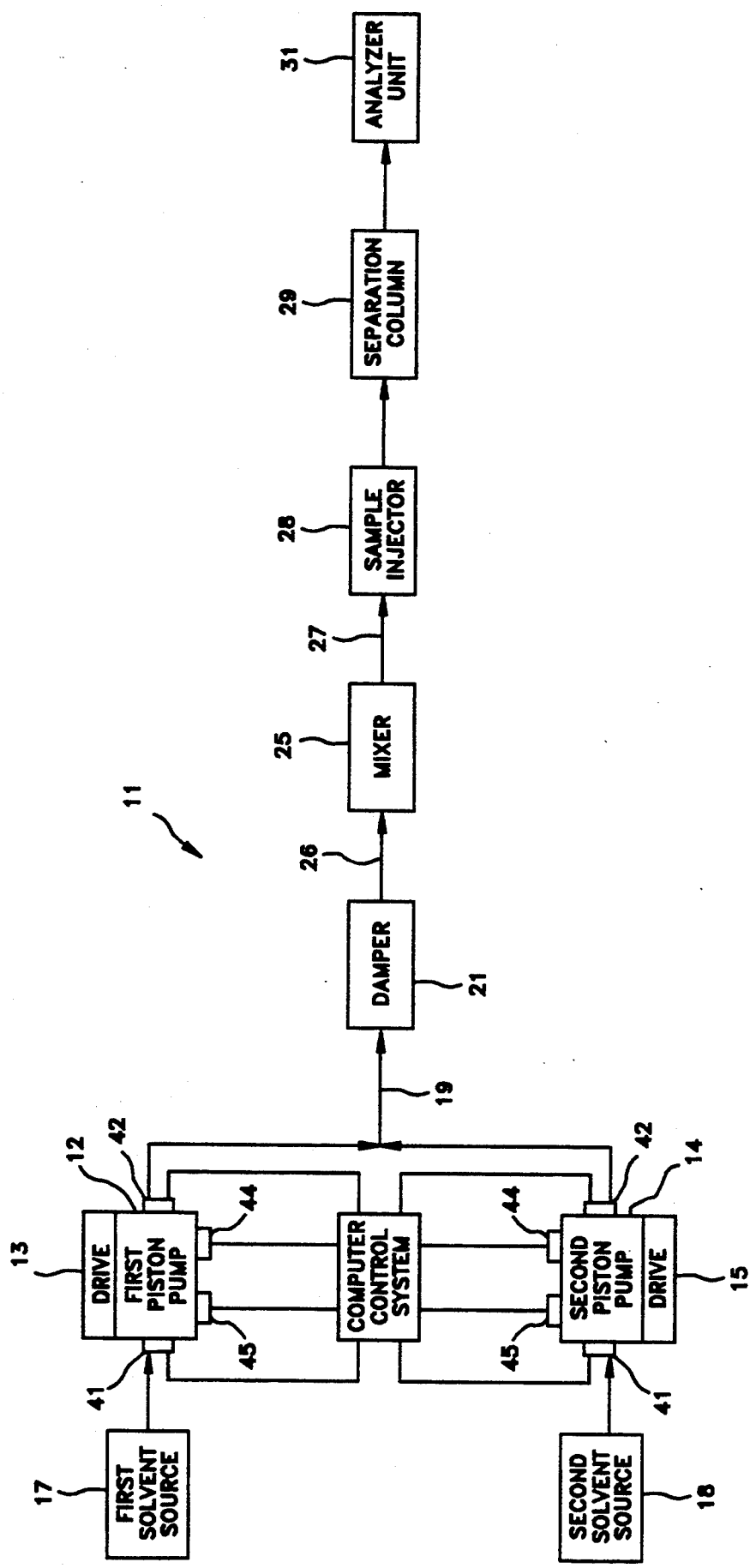
FIG. 1 is a block diagram of an HPLC system according to the invention.

An HPLC system 11 includes a first piston pump 12 operatively coupled to a stepping motor drive 13 and a second piston pump 14 operatively coupled to a stepping motor drive 15. Communicating with inlets of the first and second piston pumps 12, 14, respectively, are a first solvent source 17 and a second solvent source 18. Outlets of the first and second piston pumps 12, 14 communicate with an input 19 of a balloon-type damper.

Also included in the HPLC system 11 is a mixer 25 having an inlet connected to the outlet of the damper 21 by a feed tube 26. Connected to an outlet of the mixer 25 is a discharge tube 27 that communicates with a sample injector assembly 28. The combined output of the mixer 25 and sample injector assembly 28 is fed into a separation column 29. Receiving the output from the separation column 29 is an analyzer unit 31.

Each of the pumps 12, 14 has an inlet valve 41 communicating, respectively, with the solvent sources 17, 18 and an outlet valve 42 communicating with the damper 21. In addition, each of the pumps 12, 14 is provided with a position detector 44 for detecting piston plunger displacement and a pressure transducer 45 for detecting pumping chamber pressure. Operation of the pumps is controlled by a computer control system 51 coupled to the inlet valves 41, the outlet valves 42, the position detectors 44 and the pressure transducers 45. During operation the pumps 12, 13 produce gradient liquid solvent flow to the damper 21 and separation column 29. However, since the pumps 12, 14 are operated identically, the following will provide a detailed operating description only for the pump 12.

Figure 2:
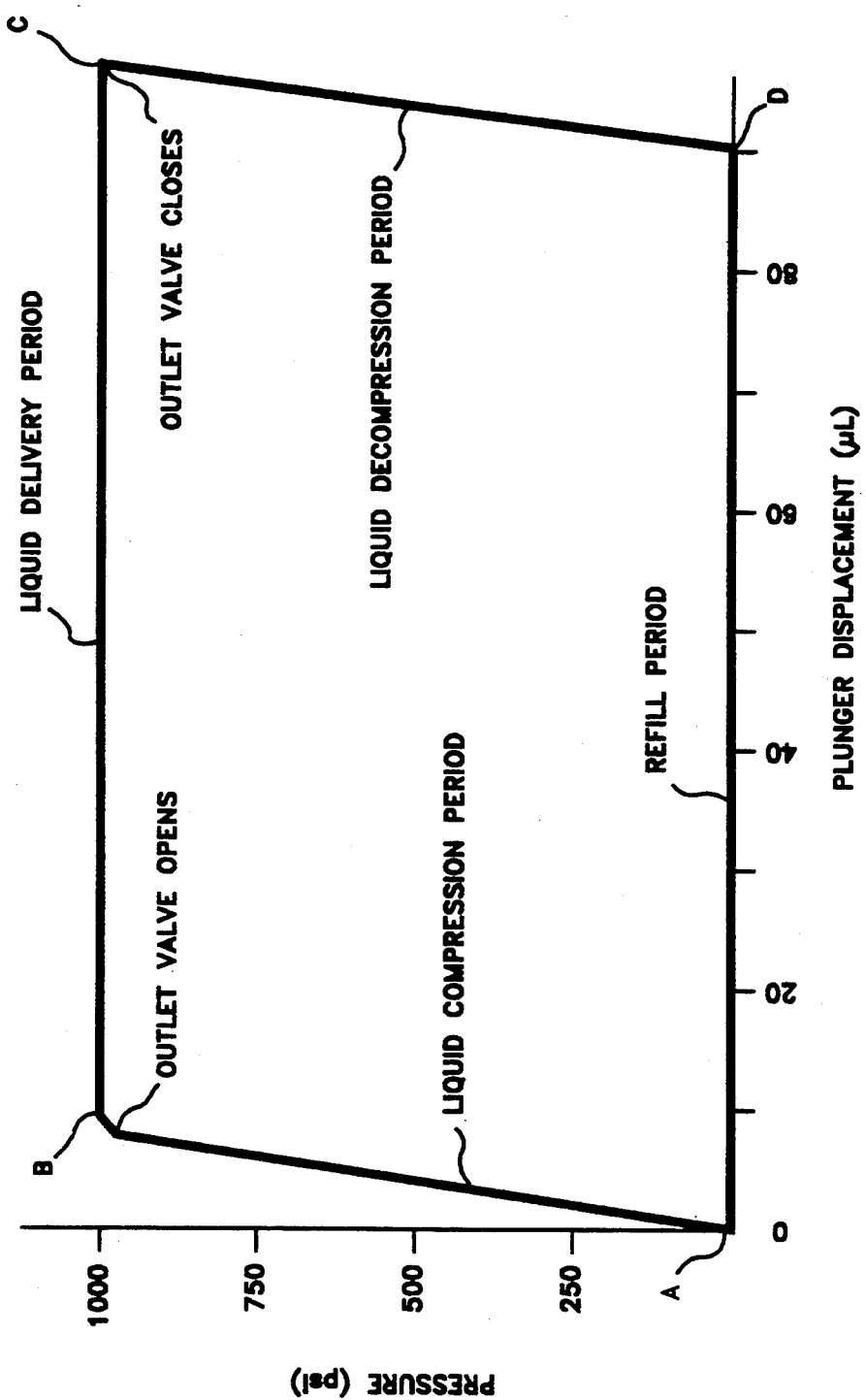
FIG. 2 is an ideal piston pump cycle diagram in which chamber pressure in psi is plotted versus piston displacement in microliters.

Illustrated in FIG. 2 is a pump cycle diagram in which chamber pressure is plotted versus piston displacement for the pump 12 if ideal operation of a perfect pump is assumed. Chamber pressure is plotted in pounds per square inch (psi) and plunger displacement, which represents length of piston stroke in volume displaced by the piston for that length, is plotted in microliters. At a point A in the pump cycle, the piston plunger begins a positive stroke which compresses liquid solvent with the inlet and outlet valves 41, 42 closed until point B when system pressure is achieved and the outlet valve 42 opens. Between points B and C of the pump's positive cycle, the piston delivers solvent through the open outlet valve 42 to the damper 21. At a point C, the outlet valve 42 closes and the piston begins its return stroke. During a period C-D, liquid solvent remaining in the chamber is decompressed until atmospheric pressure is reached at point D when the inlet valve 41 opens. Between the points D and A, the return stroke of the piston draws solvent through the open inlet valve 41 into the pump 12 from the solvent source 17. Again, assuming ideal operation, the refill stroke period D-A together with the known pumping chamber geometry and piston reciprocation rate can be used to calculate the solvent flow rate delivered by the pump 12 to the damper 21.

Figure 3:
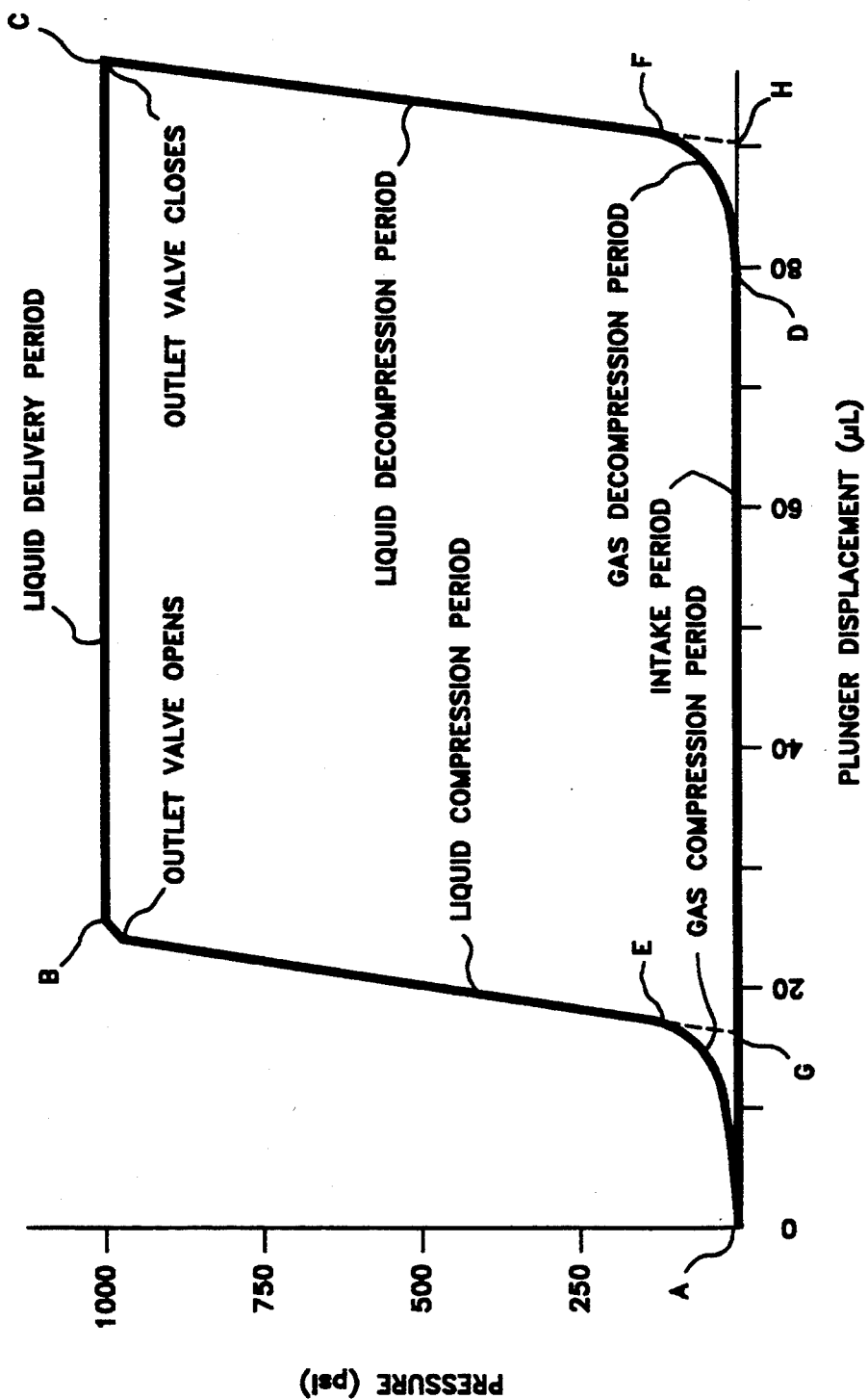
FIG. 3 is a similar diagram of an actual piston pump cycle.

A more practical pump cycle for the piston pump 12 operating under typically expected conditions is depicted in FIG. 3. Again, the portion of the curve between points A and C represents a positive piston stroke and the portion between points C and A represents a return piston stroke. Included in the positive stroke A-C is a gas compression stroke period A-E during which any gas content of the pump chamber is compressed, a liquid compression stroke period E-B during which liquid solvent in the pump chamber is compressed up to system pressure and a delivery stroke period B-C during which compressed liquid solvent is delivered through the outlet valve 42 to the damper 21. Both the inlet valve 41 and the outlet valve 42 are closed during the gas compression stroke period A-E and the liquid compression stroke period E-B, while during the delivery stroke period B-C the inlet valve 41 is closed and the outlet valve 42 is open. The return stroke C-A includes a liquid decompression period C-F during which remnant liquid solvent in the pump chamber is decompressed, a gas decompression stroke period F-D during which gasses in the pump chamber decompress and expand and an intake stroke period D-A during which the pump chamber is refilled with liquid from the solvent source 17. Both the inlet valve 41 and the outlet 42 are closed during the liquid decompression liquid stroke period C-F and the gas decompression stroke period F-D, while during the intake stroke period D-A the inlet valve 41 is open and the outlet valve 42 is closed.

During the stroke period A-E, gasses remaining in the pumping chamber are compressed into a very small volume and finally driven into solution so as to occupy a negligible portion of chamber volume. Subsequently, during stroke period E-B, liquid solvent within the pumping chamber is compressed. Conversely, during the return stroke D-A, remnant liquid solvent is decompressed during the period C-F after which remnant gasses decompress and expand to occupy all the chamber volume created by piston movement between points F and D. By projecting the substantially straight line portions of the liquid compression stroke period E-B and the liquid decompression stroke period C-F, points G and H, respectively, on the return stroke C-A are determined. The distance between points G and H represents the effective length of an intake stroke required to draw into the pump chamber at atmospheric pressure the volume of liquid solvent delivered during the delivery stroke period B-C. During each operating cycle of the pump 21, the control system 51 determines the positions G and H by performing a linear progression of chamber pressure detected by the pressure detector 45 to establish a best fit straight line for the liquid compression stroke period E-B and the liquid decompression stroke period C-F. The effective piston displacement G-H together with the known geometry of the pump chamber is used by the computer control system 51 to determine the actual liquid solvent at atmospheric pressure delivered by the pump 12 during each operating cycle.

The actual delivered liquid volume information derived in the manner described above is used by the computer control system 51 to establish a desired constant rate of solvent mass flow through the separation column 29. Initially, pump geometry is utilized to establish for the pump's piston, a stroke length and rate of reciprocation that under ideal conditions would provide a given desired rate of liquid flow to the separation column 29. Utilizing the pump parameters selected to provide the desired rate of liquid flow, the computer control system 51 determines for a predetermined operating period a desired liquid volume that would be delivered to the damper 21 and column 19 by the pump 12 if producing the desired given rate of liquid flow. Utilizing the technique described above, the computer control system 51 also determines the total actual liquid volume delivered by the pump during the predetermined operating period by summing for each cycle thereof the actual liquid volume delivered. In response to a comparing step indicating that the total actual volume delivered is different from the desired liquid volume, the control system 51 makes a compensatory change in the stroke length of the pump 12 to correct the calculated difference. For example, if the actual liquid volume is less than the desired liquid volume, the stroke length is increased to establish increased flow. Conversely, if the actual liquid volume is greater then the desired liquid volume, the stroke length is diminished to reduce flow. Correction is made in a single pump cycle if possible but can be continued for a number of subsequent cycles if necessary to establish a condition in which the total actual liquid volume delivered by the pump 12 during the given operating period is equal to the desired liquid volume that would have been delivered by a perfectly operating pump. Preferably, the desired liquid volume and actual delivered liquid volume are compared during each operating cycle of the pump 12 and the control system 51 maintains an existing volume delivery error equal to the algebraic summation of the differences between desired liquid volume and actual delivered liquid volume during each pump cycle. In addition to changing piston stroke length to compensate for delivered volume error, the computer control system 51 establishes during each pump cycle a piston reciprocation velocity that maintains for the selected stroke length the desired predetermined rate of piston reciprocation.

Figure 4:
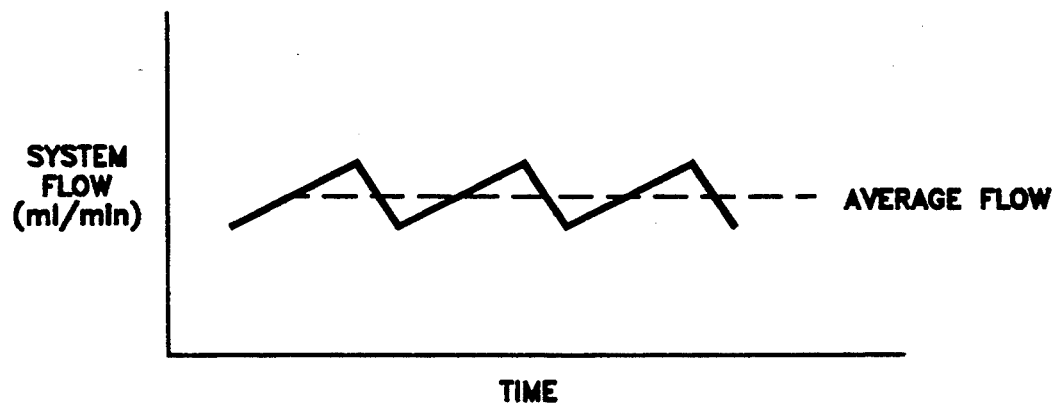
FIG. 4 is a diagram of a conventional HPLC damper operating characteristic in which output flow rate is plotted versus time.

The damper 21 functions to smooth solvent flow to the separation column 29 by accumulating liquid solvent during delivery strokes of the pump 12 and delivering solvent to the mixer 25 during refill strokes of the pump. If operating in a conventional manner, the damper output flow would assume the characteristic illustrated in FIG. 4 which plots system flow out of the damper versus time. In the saw-tooth wave illustrated, each upward leg represents a period when the damper is accumulating solvent and each downward leg represents a delivery period during which the damper is releasing solvent to the mixer 25 and column 29. Although such operation improves uniformity, FIG. 4 illustrates that conventional dampers provide a periodic flow rate that continuously varies above and below an average flow rate. The resulting periods of non-average flow are detrimental to chromatographic analysis.

Figure 5:
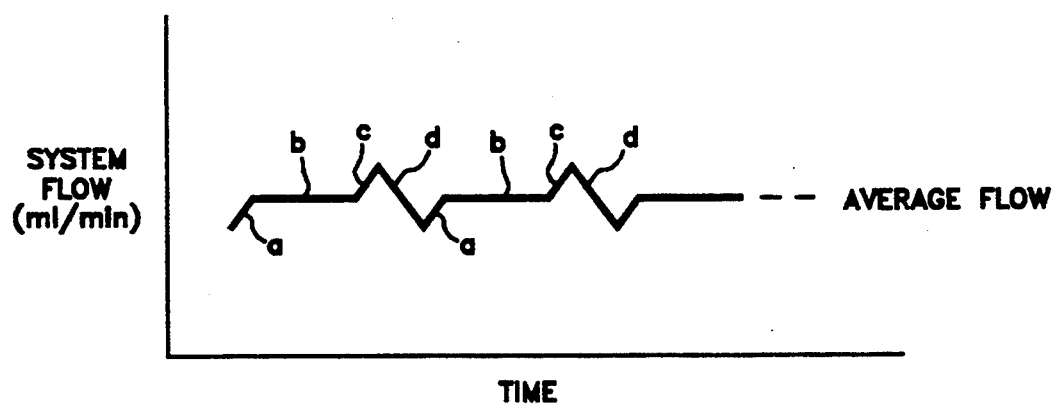
FIG. 5 is a similar diagram illustrating improved operating characteristics.

To provide a more uniform damper output flow, the computer control system 51 provides for the pump 12 two periods during which output flow rate is increased above a selected predetermined average flow rate. The increased flow rate is produced by increasing the velocity of the pump's piston during the first and second periods which occur, respectively, at the beginning of the pump's delivery stroke period B-C (FIG. 3) and at the end of the delivery stroke period. A resulting flow characteristic is illustrated in FIG. 5 in which periods a and c represent the first and second periods of increasing flow straddled by periods b during which the piston velocity is reduced to produce the average flow rate desired for the separation column 29. During the first and second periods a and c, the damper 21 is accumulating liquid, during periods b the damper is transmitting the received average flow from the pump 12 and during periods d between periods b and a, the damper 21 is delivering retained liquid solvent during refill strokes of the pump.

As shown in FIG. 5, the resultant system flow out of the damper 21 includes lengthy periods b of desired average flow separated by combined periods c-d-a of varying flow. However, if the difference between the average flow rate and the rate of the end of a period b is equal to the difference between the average flow rate and the flow rate at the beginning of periods a, the average flow during each period c-d-a will be the predetermined desired average flow.

Figure 6:
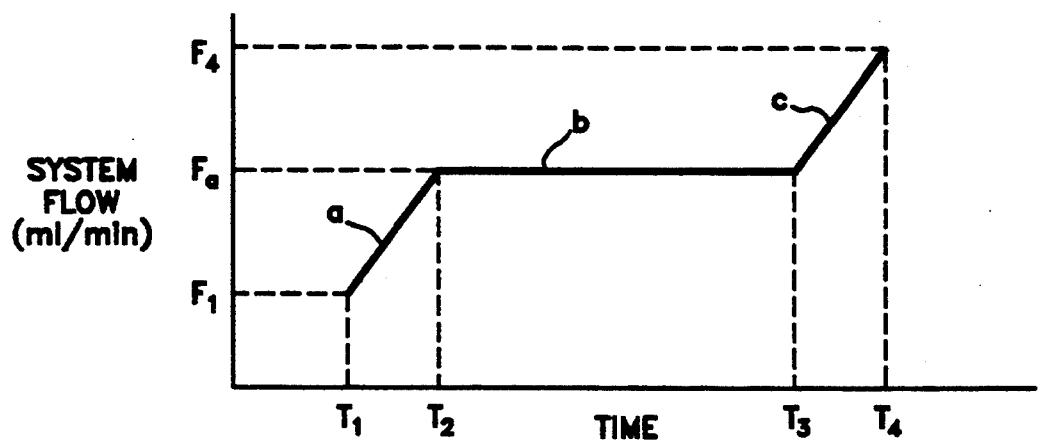
FIG. 6 is a more detailed view of a portion of the diagram shown in FIG. 5.
Figure 7:
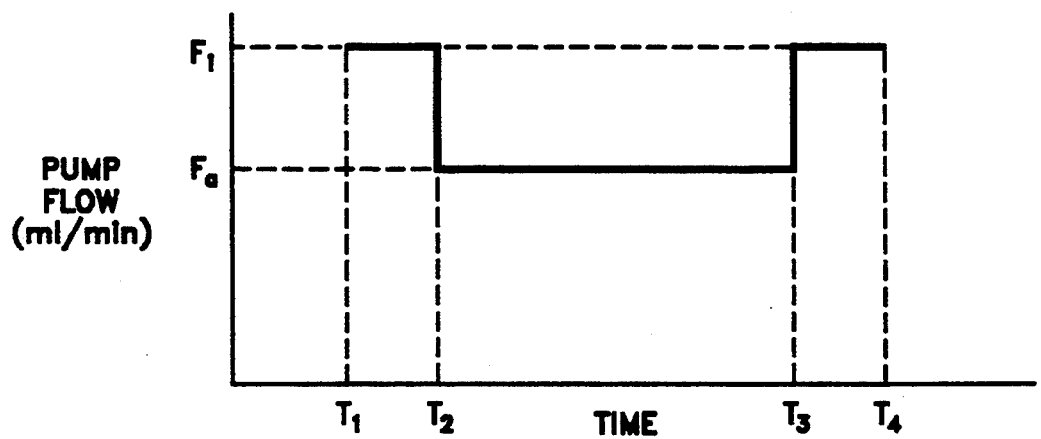
FIG. 7 is a diagram in which HPLC piston pump output flow is plotted versus time.

The first period a of increased flow preferably is at the maximum flow rate of the pump 12 and continues until the outlet flow of the damper 21 is at average flow. Then, the pump speed is changed to produce average flow during period b. The second period c of increased flow also preferably is at the maximum flow rate of the pump and begins at a time which makes the increases in system flow equal during periods a and c. The manner in which equal increases in flow are obtained will be explained in conjunction with FIGS. 6 and 7 which depict variations with time of, respectively, system flow out of the damper 21 and flow out of the pump 12. In FIGS. 6 and 7 is the time at the beginning of the first period when the outlet valve 42 opens and delivery of pressurized liquid begins to the damper 21; is the time when flow through the system has reached it's desired average value; is the time at the beginning of the second period when flow to the damper again is increased; and is the time when delivery of pressurized fluid to the damper 21 is terminated.

A conventional damper performs according to the following equation: (1) $P_d = K_d V_d$ where $P_d$ is the pressure in the damper, $V_d$ is the volume in the damper and $K_d$ is a constant based on damper design.

A conventional HPLC system which operates with laminar flow at very low Reynolds numbers performs according to the following equation: (2) $F_s = K_s P_s$ where $F_s$ is the flow rate through the system, $P_s$ is the pressure applied to the system and $K_s$ is a constant based on system configuration. Since the outlet of the damper 21 is connected to the column system, (3) $P_s = P_d$ at all times, and (4) $F_s = K_s K_d V_d$. At time $T_1$ in FIG. 6, system flow is $F_1$. The increasing system flow during interval $T_1 - T_2$ (a) is a short segment of an exponential function which may be approximated as a straight line for engineering purposes. The average flow to the system during $T_1 - T_2$ is (5) $(F_1 + F_a)/2$. The flow to the damper during $T_1 - T_2$ is (6) $F_i$. Therefore, the damper volume must increase by (7) $(F_i - (F_1 + F_a)/2)(T_2 - T_1)$ during the first interval (a) and system flow increases according to (4).

To make the second interval $T_4 - T_3$ (c) have an equal change in system flow, the change in damper volume must be equal. During that second interval (c) the average system flow is (8) $(F_a + F_4)/2$, and the flow to the damper is (9) $(F_i)$. Therefore, the damper volume must increase by (10) $(F_i - (F_a + F_4/2)(T_4 - T_3)$ and by the above noted design objective (11) $F_4 - F_a = F_a - F_1$. By combining (4), (10) and (11) we have $$T_4 - T_3 = \frac{2 F_i - F_1 - F_a}{2 F_i - F_1 - 3 F_a} (T_2 - T_1)$$

and since $F_i$, $F_1$ and $F_a$ are constants, $t_4 - T_3 = C (T_2 - T_1)$. Therefore, the length of the period (c) required to establish a damper volume change equal to that provided during period (a) can be determined and applied. That results in a combined period c-d-a (FIG. 5) having the desired average flow.

According to a preferred practical method, system pressure which with the outlet valve 42 open is substantially equal to pump chamber pressure. The system pressure which with the outlet valve 42 open is substantially equal to pump chamber pressure is detected at points $T_2$ and $T_3$ during each cycle of operation to determine if a uniform flow rate was provided during period (b). In the event that the system pressures at points $T_2$ and $T_3$ are not equal indicating a changing flow rate during period (b), the relative length of periods (a) and (c) are adjusted for a subsequent cycle to establish a more uniform flow rate during period (b). For example, if the pressure at $T_2$ is greater than the pressure at $T_3$ during a given cycle indicating decreasing flow during the period (b), the length of period (a) is decreased and the length of period (c) is increased during the subsequent cycle. Conversely, if the pressure at $T_2$ is less than the pressure at $T_3$ during a given cycle indicating increasing flow during the period (b), the length of period (a) is increased and the length of period (c) is decreased during a subsequent cycle. The time $T_1$ during each cycle is selected by detecting chamber pressure and making with the computer control system 51 an on-the-fly determination of the point E (FIG. 3) and, consequently, the time required to compress the liquid in the chamber until compressed liquid is available for delivery. The displacement point E is where the slope of the compression curve A-B is substantially equal to the substantially constant slope of the compression curve E-B during the previous pumping cycle.

Obviously, many modifications and variations of the present invention are possible in light of the above teachings. For example, by providing highly sophisticated equipment, all calculations could be performed in real time rather than by use of past data as described. It is to be understood, therefore, that the invention can be practiced otherwise than as specifically described.

What is claimed is:

1. A method of operating liquid chromatography apparatus including a piston pump having a piston reciprocable within a chamber, an inlet valve for transmitting liquid into said chamber, an outlet valve for discharging liquid from said chamber, column means receiving liquid from said outlet valve, pressure detection means for monitoring the pressure in said chamber, variable speed drive means for inducing reciprocating movement of said piston in said chamber, position detection means for monitoring the position of said piston in said chamber and computer control means for controlling the stroke length and reciprocating velocity of said piston; the method comprising the steps of:
   determining a given rate of liquid flow desired from said pump to said column means;
   establishing for said piston a predetermined stroke length and rate of reciprocation for providing said given rate of liquid flow;
   determining for each cycle of said pump a desired liquid volume that would be delivered to said column means by said pump if producing said given rate of liquid flow;
   ascertaining for each cycle of said pump the actual liquid volume delivered thereby to said column means;
   determining for a predetermined operating period of said pump the total desired liquid volume that would have been delivered to said column means by said pump if producing said given rate of liquid flow during each cycle of said predetermined operating period;
   determining the total actual liquid volume delivered to said column means by said pump during all cycles of said predetermined operating period;
   comparing said total desired liquid volume with said total actual liquid volume; and
   producing for one or more subsequent cycles of said piston, operation that produces a compensating liquid flow rate different than said given rate of liquid flow in response to a determination during said comparing step that a difference exists between said total actual liquid volume and said total desired liquid volume.

2. A method according to claim 1 wherein said operating period comprises a single cycle by said pump.

3. A method according to claim 1 wherein said comparing step comprises the steps of comparing during each cycle of said predetermined operating period said desired liquid volume with said actual liquid volume, and algebraically summing the differences therebetween for all said cycles of said predetermined operating period to thereby determine said difference.

4. A method according to claim 1 wherein said subsequent cycles are continued until a said comparing step determines that said total actual liquid volume is equal to said total desired liquid volume.

5. A method according to claim 4 wherein said producing step comprises for each said subsequent cycle the step of providing a stroke length different than said predetermined stroke length.

6. A method according to claim 5 wherein said producing step comprises the step of providing a stroke length longer than said predetermined stroke length in response to a determination that said total actual liquid volume is less than said total desired liquid volume.

7. A method according to claim 5 wherein said producing step comprises the step of providing a stroke length shorter than said predetermined stroke length in response to a determination that said total actual liquid volume is greater than said total desired liquid volume.

8. A method according to claim 1 wherein said producing step further comprises for each said subsequent cycle the step of changing the reciprocation velocity of said one piston so as to maintain said predetermined rate of reciprocation.

9. A method according to claim 8 wherein said ascertaining step comprises the step of ascertaining for each said cycle the volume of liquid at atmospheric pressure delivered by said pump to said column means.

10. A method according to claim 9 wherein during each operating cycle said piston completes a positive stroke including a gas compression stroke period during which any gas in said chamber is compressed while said outlet valve and said inlet valve are closed, a liquid compression stroke period during which liquid in said chamber is compressed while said outlet valve and said inlet valve are closed and a delivery stroke period during which liquid is delivered to said column means while said outlet valve is open and said inlet valve is closed; and a return stroke including a liquid decompression stroke period during which liquid in said chamber is decompressed while said outlet valve and said inlet valve are closed, a gas decompression stroke period during which any gas in said chamber is decompressed while said outlet valve and said inlet valve are closed, and an intake stroke period during which liquid is received by said chamber while said outlet valve is closed and said inlet valve is open.

11. A method according to claim 10 wherein said inlet valve comprises a valve that closes in response to a pressure in said chamber above atmospheric and opens in response to substantially atmospheric pressure in said chamber; and said ascertaining steps comprise the step of calculating an effective length of a return stroke required to draw in a volume of liquid at atmospheric pressure equal to the volume delivered by said pump during said cycle.

12. A method according to claim 11 wherein said calculating step comprises the steps of calculating the length of said delivery stroke period plus the length of said liquid compression stroke period less the length of said liquid decompression stroke period.

13. A method according to claim 12 wherein said calculating steps comprise the steps of determining the lengths of said gas compression and said gas decompression stroke periods.

14. A method according to claim 12 wherein said calculating steps comprise the steps of correlating detected pressures in said chamber with positions of said piston during said gas and liquid compression stroke periods and during said gas and liquid decompression stroke periods.

15. A method according to claim 14 wherein said calculating step further comprises the steps of finding a substantially linear progression of the information derived during said correlating steps.

16. A method according to claim 1 wherein said apparatus includes damper means between said pump and said column means, said inlet valve transmits liquid into said chamber in response to a pressure therein less than a given value, and said outlet valve discharges liquid from said chamber to said damper means in response to a pressure in said chamber greater than a second value substantially higher than said first value, and comprising the further steps of:
  detecting a delivery period during which said outlet valve is delivering liquid from said chamber;
  establishing for said piston during an initial portion of said delivery period a first velocity substantially greater than said predetermined velocity;
  establishing for said piston during a final portion of said delivery period a second velocity substantially greater than said predetermined velocity; and
  establishing for said piston during an intermediate portion of said delivery period said predetermined velocity.

17. A method according to claim 16 wherein said establishing steps produce a first volume increase in said damper means during said initial portion of said delivery period, substantially no volume change in said damper means during said intermediate portion of said delivery period, and a second volume increase in said damper means during said final portion of said delivery period.

18. A method according to claim 17 wherein said first velocity is substantially equal to said second velocity.

19. A method according to claim 18 wherein said first volume increase is substantially equal to said second volume increase.

20. A method according to claim 19 wherein said final portion of said delivery period is longer than said initial portion of said delivery period.

21. A method according to claim 20 wherein each of said first velocity and said second velocity is the maximum velocity of said piston producible by said variable speed drive means.

22. A method of operating liquid chromatography apparatus including a piston pump having a piston reciprocable within a chamber, an inlet valve for transmitting liquid into said chamber in response to a pressure in said chamber less than a first value, an outlet valve for discharging liquid from said chamber in response to a pressure in said chamber greater than a second value substantially greater than said first value, damper means receiving liquid from said outlet valve, column means receiving liquid from said damper means, pressure detection means for monitoring the pressure in said chamber, variable speed drive means for inducing reciprocating movement of said piston in said chamber and computer control means for controlling the reciprocating velocity of said piston; the method comprising the steps of:
  determining a given rate of liquid flow to said column means;
  determining for said piston a predetermined velocity for providing said given rate of liquid flow;
  detecting a delivery period during which said outlet valve is delivering liquid from said chamber;
  establishing for said piston during an initial portion of said delivery period a first velocity substantially greater than said predetermined velocity;
  establishing for said piston during a final portion of said delivery period a second velocity substantially greater than said predetermined velocity; and
  establishing for said piston during an intermediate portion of said delivery period said predetermined velocity.

23. A method according to claim 22 wherein said establishing steps produce a first volume increase in said damper means during said initial portion of said delivery period, substantially no volume change in said damper means during said intermediate portion of said delivery period, and a second volume increase in said damper means during said final portion of said delivery period.

24. A method according to claim 23 wherein said first velocity is substantially equal to said second velocity.

25. A method according to claim 24 wherein said first volume increase is substantially equal to said second volume increase.

26. A method according to claim 24 wherein said final portion of said delivery period is longer than said initial portion of said delivery period.

27. A method according to claim 24 wherein each of said first velocity and said second velocity is the maximum velocity of said piston producible by said variable speed drive means.

28. A method according to claim 23 wherein said first volume increase is substantially equal to said second volume increase.

* * * * *